(12) United States Patent
Li et al.

(10) Patent No.: US 8,566,039 B2
(45) Date of Patent: Oct. 22, 2013

(54) METHOD AND SYSTEM TO CHARACTERIZE TRANSCRIPTIONALLY ACTIVE REGIONS AND QUANTIFY SEQUENCE ABUNDANCE FOR LARGE SCALE SEQUENCING DATA

(75) Inventors: Xitong Li, Mountain View, CA (US); Kenneth Stineman, San Jose, CA (US)

(73) Assignee: Genomic Health, Inc., Redwood City, CA (US)

( * ) Notice: Subject to any disclaimer, the term of this patent is extended or adjusted under 35 U.S.C. 154(b) by 1543 days.

(21) Appl. No.: 12/121,412

(22) Filed: May 15, 2008

(65) Prior Publication Data
US 2009/0287420 A1 Nov. 19, 2009

(51) Int. Cl.
*G01N 33/48* (2006.01)
*G06F 19/00* (2011.01)

(52) U.S. Cl.
USPC .............................................. 702/19; 702/20

(58) Field of Classification Search
None
See application file for complete search history.

(56) References Cited

U.S. PATENT DOCUMENTS

| | | | |
|---|---|---|---|
| 7,704,687 B2 | 4/2010 | Wang et al. | |
| 2003/0187587 A1* | 10/2003 | Swindells et al. | 702/19 |
| 2005/0221341 A1 | 10/2005 | Shimkets et al. | |
| 2010/0260827 A1* | 10/2010 | Mani et al. | 424/450 |

OTHER PUBLICATIONS

Dunham et al, "The DNA sequence of human chromosome 22" (Nature, vol. 402 (1999) pp. 489-495).*

* cited by examiner

*Primary Examiner* — Anna Skibinsky
(74) *Attorney, Agent, or Firm* — Kilpatrick Townsend & Stockton LLP

(57) ABSTRACT

This invention provides a quantitative method to determine transcriptionally active regions and quantify sequence abundance from large scale sequencing data. The invention also provides a system based on reference sequences to design and implement the method. The system processes large scale sequence data from high throughput sequencing, generates transcriptionally active region sequences as necessary, and quantifies the sequence abundance of the gene or transcriptionally active region. The method and system are useful for many analyses based on RNA expression profiling.

39 Claims, 6 Drawing Sheets

S1: CAAAGAAATCCAGCGTCACTAGGTCAGCTAAGCCGAA
S2: GGCACAAAGAAATCCAGCGTCACTAGGTCAGCTAAGCCGAAAAAATGT
S3:                       ATGTGTGCCTGCGCCTCCTCGCCTCGCCTCATCGATGACAT
S4:     TCCAGCGTCACTAGGTCAGCTAAGCCGAAAAATGTGTGCCTGCGCTCCTCGCCTCGCCTCATCGAT
S5:          GGTCAGCTAAGCCGAAAAATGTGTGCCTGCGCCTCCTCGCCTCGCCTCATCGATGAC
S6:                GCTAAGCCGAAAAATGTGTGCCTGCGC
S7:        TCACTAGGTCAGCTAAGCCGAAAAAA
S8:                          TGTGCCTGCGCTCCTCGCCTCATC
R: GGCACAAAGAAATCCAGCGTCACTAGGTCAGCTAAGCCGAAAAATGTGTGCCTGCGCTCCTCGCCTCATCGATGACAT

FIG. 2

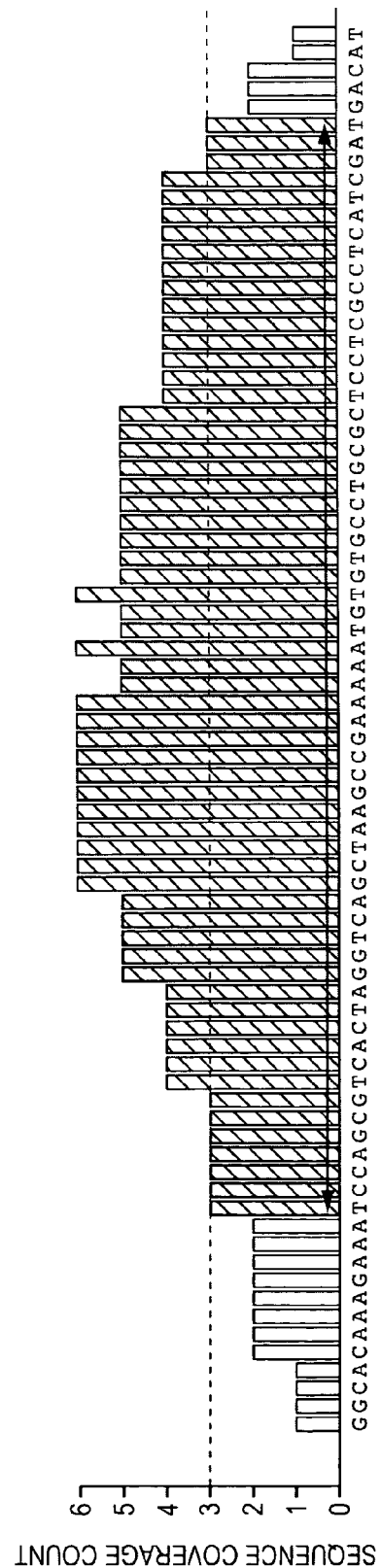

FIG. 3

|       |                          |
|-------|--------------------------|
| EST1  | ----TAAAAGGAGGCG---- |
| EST2  | ------AAAGGAGGC----- |
| EST3  | -----AAAAGGAGGCGC--- |
| EST4  | -------AAGGAGGC----- |
| EST5  | ---TTAAAAGGAGGC---- |
| Genome Region | CAGTTAAAAGGAGGCGCCTG |

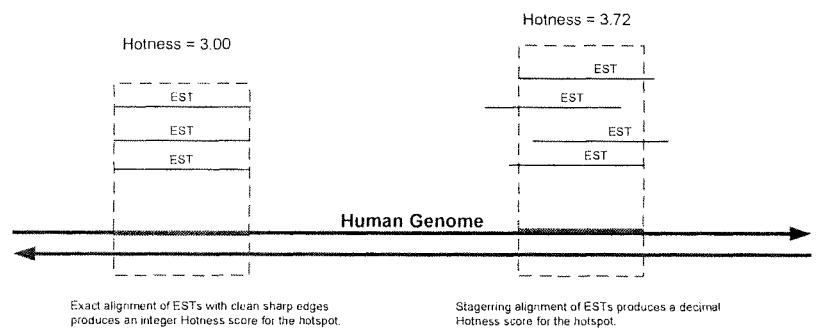
Figure 6. Graphical representation of EST alignment to reference sequence

METHOD AND SYSTEM TO CHARACTERIZE TRANSCRIPTIONALLY ACTIVE REGIONS AND QUANTIFY SEQUENCE ABUNDANCE FOR LARGE SCALE SEQUENCING DATA

FIELD OF THE INVENTION

This invention relates generally to a sequence data analysis system using methods for processing nucleic acid sequencing output-with a reference sequence based design to identify transcriptionally active regions and quantify the sequence abundance which can be used for expression profiling analysis.

DESCRIPTION OF THE RELATED ART

DNA sequencing technology has played a key role in the advancement of genomic study and research for health sciences for more than 10 years. At the same time, the completion of the human genome sequencing project has been recognized as one of the most significant milestones for research and drug development. Recently several next generation sequencing technologies have made it possible to read billions of nucleotides in a single experiment. The availability of billion nucleotide scale sequencing and its expected cost reduction has expanded the potential applications of sequencing to area such as RNA expression profiling and genome scale biomarker discovery that historically have not been possible.

RNA expression profiling is used by researchers to measure the quantities of many different RNAs transcribed from the genome in various cell types and cell growth stages. It is also used as a diagnostic method to help predict a patient's risk for disease and response to treatment. Common forms of RNA expression profiling include gene expression profiling, exon expression profiling, non-coding RNA expression profiling, and whole transcriptome profiling. Methods of RNA expression profiling are often performed in high throughput platforms and typically comprises the following steps:
1. Isolate RNAs from a biological sample.
2. Convert the RNAs isolated into to their complementary DNAs (cDNAs) typically through reverse transcription.
3. Quantify the level of cDNAs using high throughput platform such as microarray and large scale quantitative PCR (QPCR). Recently large scale sequencing been utilized for cDNA quantification as well.
4. Employ a quantitative analysis method to analyze the RNA level association with biological processes (e.g. disease).

The cost of DNA sequencing technology has been trending down quickly and the trend will continue for decades to come. Sequencing technology is becoming the preferable choice for expression profiling due to its higher throughput, higher accuracy, and more flexibility for small and non-coding RNA expression profiling. However, application of high throughput sequencing for RNA expression profiling and genome scale biomarker discovery may encounter issues in the following areas:

Transcriptionally active region identification: In order to profile RNA expression, RNA sequences or their equivalent DNA sequences to be used for the expression profiling analysis need to be determined. In this application, these RNA sequences or their equivalent DNA sequences for the expression profiling analysis are defined as transcriptionally active regions. Typical transcriptionally active regions may be represented by RNA sequences, cDNA sequences, exon sequences, and non-coding RNA or equivalent DNA sequences. Within this context, the transcriptionally active regions can be conceptualized as the transcribed regions of the human genome. The genes used for RNA expression profiling have been mostly protein coding sequences in the past. In recent years, accumulating evidence has shown non-coding DNA plays a vital role in the regulation of gene expression during normal and disease processes. To find non-coding sequences as biomarkers and profile their expressions become desirable and critical for many genomics studies. However, for the less known non-coding RNAs including microRNA and many other small RNAs, their genomic transcribed regions are often not well defined. The sequencing output sequences for these non-coding regions are often not well-aligned due to either biological or technical reasons. This inexact mapping makes it very difficult to derive the transcriptionally active regions for expression profiling analysis.

Sequence abundance quantification: When using sequencing for RNA expression profiling, there is no well-defined method to quantify the gene or transcriptionally active region sequence abundance. In high throughput setting, quantifying the number of nucleotide sequences is a challenge because the output sequences usually do not align exactly to the reference sequences even though they are derived from the same gene. This often results from many well-known biological processes such as alternative splicing, alternative transcription initiation, alternative transcription termination, RNA degradation, etc. Additionally, the reverse transcription to convert RNAs into complementary DNAs (cDNAs) for sequencing is often partial or incomplete. As a result, the output sequences generated by sequencing even for the same gene are often heterogeneous, have various length and/or various sequence composition as the case illustrated in FIG. 2. This inexact mapping of sequencing output sequences makes the quantification of the RNA levels for the genes or transcriptionally active regions difficult and not straightforward.

Computation intensity: Many sequence analyses such as genome sequence assembly or EST sequence clustering can be fundamentally transformed into iteration of the alignment of two sequences, i.e. pairwise sequence alignment. For large sequence data analysis this pairwise sequence alignment usually is the limiting factor. The computing intensity and cost is high due to the complexity of sequence alignment algorithms such as Needleman-Wunsch algorithm (Needleman and Wunsch 1970), Smith-Waterman algorithm (Smith and Waterman 1981), or other similar algorithms. An efficient method to reduce computing intensity for pairwise sequence alignment is highly desirable for large scale sequence analyses.

SUMMARY OF THE INVENTION

Here we provide a sequence data analysis system using a reference sequence based design to implement the method for transcriptionally active region identification and sequence abundance quantification. The sequence data analysis system uses a method developed to process sequencing output sequences to find transcriptionally active regions as necessary and quantify the transcriptionally active region sequence abundance, which can be used for expression profiling analysis.

Another object of the present invention is to provide a quantitative method to define a non-coding transcriptionally active region given the inexact aligned sequences from high throughput sequencing. The method can be implemented in a computing system that discovers the transcriptionally active regions with adjustable parameters from the high throughput sequencing data.

Yet another object of the present invention is to provide a method to quantify the inexact mapped output sequences for a given gene or transcriptionally active region sequence and generate a quantitative abundance score that can be used for expression profiling analysis.

In one embodiment of the present invention, a method is provided for discovery of transcriptionally active regions. In this method, sequences outputted by sequencing equipment and a reference sequence are provided and the output sequences are aligned to the reference sequences. The sequence alignments are parsed and transformed into reference sequence based coordinates. A coverage count is then calculated for each nucleotide position in the reference sequence and a contiguous reference sequence region is located where the coverage count is equal to or greater than a threshold.

In another embodiment of the present invention, a system is disclosed for discovery of transcriptionally active regions. The system comprises a first processor for aligning sequences outputted by sequencing equipment and a reference sequence, a database for collecting reference sequence based coordinates, a second processor for calculating a coverage count for each nucleotide position in said reference sequence and locating a contiguous reference sequence region where the coverage count is equal to or greater than a threshold, and a computer output device for displaying transcriptionally active region profiles.

In another embodiment of the present invention, a method is provided for RNA expression profiling. In this method, sequences outputted by sequencing equipment and a reference sequence are provided and the output sequences are aligned to the reference sequences. The sequence alignments are parsed and transformed into reference sequence based coordinates. A coverage count is then calculated for each nucleotide position in the reference sequence and a contiguous reference sequence region is identified where the coverage count is equal to or greater than a threshold. Once the coverage count for each nucleotide in the transcriptionally active regions is determined an abundance score is calculated for each transcriptionally active region.

In another embodiment of the present invention, a system is disclosed for RNA expression profiling. The system comprises a first processor for aligning sequences outputted by sequencing equipment and a reference sequence, a database for collecting reference sequence based coordinates, a second processor for calculating a coverage count for each nucleotide position in said reference sequence and locating a contiguous reference sequence region where the coverage count is equal to or greater than a threshold, a third processor for calculation of abundance scores; and a computer output device for displaying RNA expression profiles.

In another embodiment of the present invention, a method is provided for identifying diagnostic and prognostic markers of disease. In this method, sequences outputted by sequencing equipment from normal and disease samples and a reference sequence are provided and the output sequences are aligned to the reference sequences. The sequence alignments are parsed and transformed into reference sequence based coordinates. A coverage count is then calculated for each nucleotide position in the reference sequence and a contiguous reference sequence region is identified where the coverage count is equal to or greater than a threshold. Once the coverage count for each nucleotide in the transcriptionally active regions is determined, an abundance score is calculated for each transcriptionally active region in both the normal and disease samples. From this data, differential expression patterns of transcriptionally active regions are identified between normal and disease samples.

BRIEF DESCRIPTION OF THE FIGURES

FIG. 2 illustrates the alignment of output sequences against a reference sequence SEQ ID NOS 1-9, respectively in order of appearance).

FIG. 3 illustrates how a high coverage sequence region is identified and its abundance score calculated using the sequence alignments in FIG. 2 (SEQ ID NO: 9).

FIG. 6 illustrates an example of ISE transcriptionally active regions with an integer abundance score.

DETAILED DESCRIPTION OF THE INVENTION

Figure 1:
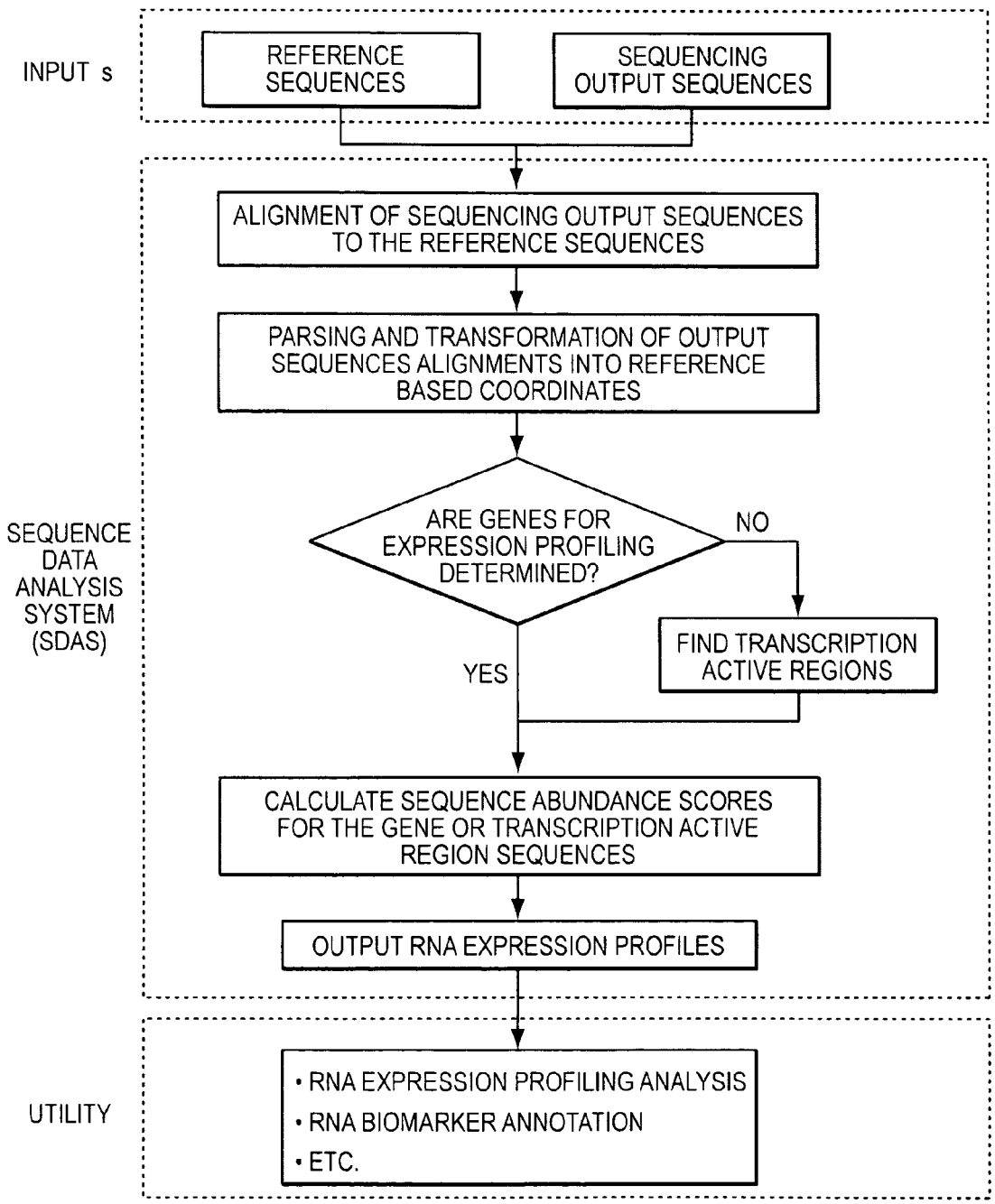
FIG. 1 is a flow chart of the sequence data analysis processes.

RNA levels from biological samples are routinely quantified on high throughput platforms such as microarray and QPCR instruments for expression analysis. As the cost of sequencing technology goes down, the application of sequencing to RNA quantification and expression profiling becomes attractive. Two technical hurdles currently make the analysis difficult when applying sequencing for expression profiling. 1) Quantification of the RNA level according to the sequencing output reads is not well defined, and 2) Non-coding gene sequences are not well defined.

The instant patent application, discloses a method to quantify RNA levels, and a method to define the transcriptionally active regions at single nucleotide resolution. The transcriptionally active regions thus defined can be used as surrogates for non-coding genes for expression profiling analysis.

Expression profiling is intended to accurately determine the RNA abundance for a given gene. In microarray, the abundance is measured by hybridization signal. In QPCR, the abundance is measured by the nucleotide amplification fractional cycle number (Ct or Cp) to reach a threshold. In sequencing, the abundance is measured by sequence count. From the technology perspective, the abundance measurement accuracy in theory should be in increasing order:

Microarray<<QPCR<<Sequencing

However, no known method has provided a good solution for sequence abundance counting, especially for non-coding gene targets. The sequence data analysis system of the instant application provides a solution to this problem.

Because most of the non-coding gene regions have been loosely defined; non-coding genes pose another challenge for expression profiling. In the sequence data analysis system of the instant application, a quantitative solution is provided to clearly define a transcriptionally active region which can be used as a surrogate for non-coding genes, especially where the start and end positions for most non-coding genes are not well-characterized.

Sequence Data Analysis System Design based on Reference Sequence Coordinates

Sequence analysis is the core task for the sequence data analysis system disclosed herein. In order to reduce the computing cost associated with pairwise sequence alignment, we designed a reference sequence based coordinates that effectively transform the pairwise sequence alignments into simpler and faster coordinate comparison. The principle behind the design is to anchor large set of sequences onto reference sequences, represent each sequence with its coordinates based on the positions of its alignment to the reference sequences, and perform the coordinate comparisons. One simple implementation is to use a pair of the reference sequence nucleotide position indices as the coordinates to represent a sequence start and end positions. With this implementation, a pairwise sequence alignment task can often be converted into a task to determine whether the two sequence fragments anchored onto reference sequences overlap or not. For example, given the two sequences, e.g. SequenceA and SequenceB, with the two following reference coordinates:

SequenceA: StartA, EndA

SequenceB: StartB, EndB the following Boolean logic or its equivalent can be used for the overlap query:

Overlap Query Form 1:

( StrandA > StrandB AND NOT (StrandA >= EndB AND EndA >= EndB) )
OR
( StrandA < StrandB AND NOT (StrandB >= EndA AND EndB >= EndA) )
OR
( StrandA = StrandB )

One particularly useful constraint on the reference coordinates is to implement them in a way that the start position is always less than or equal to the end position, or equivalently that the start position is always greater than or equal to the end position. Throughout this application, the former implementation is used and implied as an example to illustrate. However the latter implementation should work equally well. With this constraint, the start and end positions in the coordinates are relative to the anchoring reference sequences indices and do not correlate to biological start or end information such as transcription start or end. With this start-end position constraint, the overlap query can be much simplified into the following Boolean logic:

Overlap Query Form 2:

( EndA >= StartB )
AND
( StartA <= EndB )

which effectively reduce the computation complexity associated with sequence overlap query when implemented.

The overlap Boolean logic above assumes minimum overlap length is one sequence base, i.e. two sequences share at least one bases. To achieve more flexibility control on minimum overlap length (minOverlapLength), an adjustment on the coordinates can be used and the overlap Boolean logic can take the following form with this start-end position constraint:

Overlap Query Form 3:

( EndA − (minOverlapLength − 1) >= StartB + (minOverlapLength − 1) )
AND
( StartA + (minOverlapLength − 1) <= EndB − (minOverlapLength − 1) )

In the instant sequence data analysis system, the overlap query form 2 was implemented as the default. However, the overlap query based on the coordinate comparison in any forms mentioned above can be executed much faster than most known sequence alignment method. The following computing time complexity estimations illustrate the benefit of reference sequence coordinates.

To compare each sequence from one dataset to each sequence from a second dataset given two sequence datasets with size of N and M, the computing time complexity for pairwise sequence alignments is approximated by $O(N*M)$. When N is about the same size of M, this is essentially a $O(N^2)$ algorithm. Whereas the computing time complexity for coordinate comparison method is dominantly demanded by sequence alignment to the reference sequence and approximated by $O(N+M)$. It is essentially a $O(N)$ algorithm when N is about the same size of M. Therefore when sequence data are large, it is much preferable to substitute pairwise sequence alignments with coordinate comparisons.

Besides the computing time complexity benefit for sequence analysis, reference sequence coordinates provide other benefits include 1. Data storage benefit. Raw sequence data require much larger storage space than the coordinates representing the sequences.
2. Analysis benefit for new sequence dataset. When a new sequence dataset is to be analyzed with the existing dataset, the computing demand is limited to the alignment of new sequences to reference sequences and the output of coordinates for analysis.
3. Computing benefit for high sequence coverage region discovery and sequence abundance score calculation as described below.
4. Locality of information benefit. When implemented in a computing system, the reference coordinates can often be indexed. Using indices allows rapid retrieval and computation of nearby sequences in memory or disk.

With this design principle, a sequence data analysis system was developed to implement the instant method for RNA expression profiling (FIG. 1). The system supports reference sequences and sequencing output sequences as inputs. These two inputs are described as follows.

Reference Sequences

The sequence data analysis system take two inputs. One input is the reference sequences as described above. The reference sequences for sequence data analysis system could be any set of sequences that that are deemed appropriate for anchoring the sequencing output sequences. For example, in a biological setting, reference sequences could be a set of genomic sequences, RNA or cDNA sequences, or even artificial sequences. Reference sequences are pre-determined inputs to the RNA expression profiling system. In one embodiment, the reference sequences implemented in the system are the whole human genome sequences. However, in cases where there are no good existing references, they can be the assembled consensus sequences derived from sequencing output sequences through sequence assembly tools such as Phrap.

Sequencing Output Sequences

Sequencing output sequences in this document refer to the sequences outputted by sequencing equipment typically in a high throughput setting for RNA expression profiling purpose. However they could be any sequence dataset for abundance profiling. Sequencing output sequences are another input to the sequence data analysis system.

The system transforms sequencing output sequences into reference based coordinates, determines the transcriptionally active region sequences as necessary, and quantifies and outputs the abundance scores for the transcriptionally active region sequences. Each process is described as follows.

Alignments of Sequencing Output Sequences to Reference Sequences

Given the inputs of sequencing output sequences and the reference sequences, the sequence data analysis system first aligns the output sequences to the reference sequences by sequence alignment tools. In one embodiment, a linux GMAP program (Wu T, and Watanabe C 2005) was utilized to align all the output sequences to human genome reference sequences. Other sequence alignment tools for alignments of output sequences to reference sequences include BLAT, BLAST, FASTA, and clustalw. An illustration of the alignments of output sequences to the reference sequences is shown in FIG. 2.

Parsing and Transformation of Sequence Alignments into Reference Sequence Based Coordinates As described above, the reference coordinates for the sequencing output sequences are based on the nucleotide position indices of the reference sequences. In our implementation, the reference sequence nucleotide position indexing is 1-based, i.e., the first nucleotide position in the reference sequences is 1. Other indexing including 0-based indexing would work as well. For the instant sequence data analysis system, whole human genome sequences were used as the reference sequences. The human genome sequences for sequence data analysis system are naturally partitioned into 22 autosomal chromosome sequences (with naming convention of chr1, chr2, . . . , and chr22) plus chromosome X (chrX), chromosome Y (chrY), and a technical chromosome unknown (chr_unknown) to capture certain human genome sequences that can not mapped to any chromosome yet. Since human chromosomes are double stranded, the strandedness information is also captured for reference sequences and the sequencing output sequences coordinates. Therefore from the alignment outputs four components are parsed out; namely chromosome, strand, start position, and end position for each sequencing output sequence according to its alignment onto the reference sequences, and then formatted into the reference coordinates. Given the two output sequences, e.g. SequenceA and SequenceB, with the reference coordinates after parsing and formatting will be:

SequenceA: ChromosomeA, StrandA, StartA, EndA

SequenceB: ChromosomeB, StrandB, StartB, EndB

As described above, these coordinates are 1-based on reference sequences, and a start-end constraint (Start is always less than or equal to End) has been implemented. With these coordinates, the default overlap query form 2 (described above) for sequence analysis will take the following format with added constraints in Boolean logic:

Overlap Query Form 4:

( ChromosomeA = ChromosomeB )
AND
( StrandA = StrandB )
AND
( EndA >= StartB )
AND
( StartA <= EndB )

The above form is the logic for our overlap query implementation for most genome scale sequence analyses.

Determination of Transcriptionally Active Regions

Genes in RNA expression profiling are transcriptionally active regions on the reference sequences, e.g. human genome. Sometimes a set of target genes are predetermined for an RNA expression profiling study. When a set of target genes are provided, the sequence data analysis system will skip the transcriptionally active region determination step and use the pre-determined gene sequences for the following steps. Alternatively, for expression profiling involving large scale transcriptome analysis, e.g. whole transcriptome, a comprehensive set of target genes (especially for the non-coding sequences) is not pre-determined and needs to be identified as a post-sequencing process. In the cases where the target genes are not defined before the sequencing study, the transcriptionally active regions will be defined by the sequence data analysis system and used as the gene surrogates for expression profiling analysis. The way sequence data analysis system finds transcriptionally active regions is based on the sequencing output sequences. However due to the inexact mapping of sequencing output sequences to the reference sequences, it is difficult to find transcriptionally active region sequences with confidence especially for non-coding gene regions. In order to find transcriptionally active regions with higher confidence, in the sequence data analysis system a search for high coverage sequence regions (i.e., the regions that have many sequencing output sequences aligned) is conducted on the reference sequences. The underlying reasoning is that the higher the coverage by sequencing output sequences, the more likely the reference sequence regions transcribe biologically. Therefore, the instant sequence analysis application discloses a quantitative method that is implemented in a computing system for high coverage sequence region discovery in a high throughput setting as described here.

Once the sequencing output sequences have been aligned to the reference sequences, for each nucleotide position in reference sequence a coverage count is calculated and a count histogram can be generated (FIG. 3). Then a high coverage region is determined quantitatively by locating the contiguous reference sequence region where the coverage count is equal to or greater than a threshold (FIG. 3). The high coverage regions discovered thus are the transcriptionally active regions for the following RNA expression profiling analysis.

In the sequence data analysis system, a coverage count threshold of 3 was implemented in the sequence data analysis system. However, the coverage count threshold could be any fractional or integer number greater than or equal to zero In the sequence data analysis system, a minimal length constraint was also implemented for discovery of the high coverage regions. In the instant implementation, the minimal length cutoff is 20 nucleotides. However it could be any fractional or integer numbers greater than or equal to zero.

In one embodiment, by implementing the high coverage sequence regions discovery algorithm in a C++ program, all the EST transcriptionally active regions, or "hotspots", were found within all known gene intron regions for the high throughput sequence data (Li, et.al., 2007)

The high coverage sequence regions thus discovered are the transcriptionally active regions as surrogates for genes for the abundance score calculation and RNA expression profiling analysis.

Calculation of Abundance Scores

Once all sequencing output sequences are aligned onto the reference sequence, the coverage count for each nucleotide in the target genes or transcriptionally active regions can be calculated. An abundance score (AS) is calculated for each gene or transcriptionally active region with the following formula (FIG. 3)

$$AS = \frac{\text{Sum of coverage count for each nucleotide in the transcription active region}}{\text{Length of the transcription active region}}$$

In one embodiment, the transcriptionally active region discovery algorithm was implemented and the abundance scores were calculated for the transcriptionally active sequence regions found through a C++ program for all the EST transcriptionally active regions within all known gene intron regions for the high throughput sequence data (Li, et al., 2007)

Output for Transcriptionally Active Region Profiles

After the calculation of abundance scores, the system will output them along with the genes pre-determined or transcriptionally active regions discovered as the expression profiles. They can then be used for further RNA expression profiling analyses or transcriptionally active region annotation.

For the outputs of the sequence data analysis system, an SQL relational database management system was utilized to store the RNA expression profiles. Implementation using a database solution effectively takes full advantage of database server enterprise hardware to meet the high throughput bioinformatics computing demands that have historically been solved by C++ or JAVA numeric programming. With the SQL server's built-in algorithms, use of constrained data types for genomic coordinates (integer types for start and end nucleotide positions), and indexing capabilities, the overlap queries for sequences analysis can operate efficiently on indexed integers. This SQL database based approach has several advantages:
1. SQL databases built-in indexing features significantly improve the efficiency of genomic comparisons which historically demanded complex programming and data partitioning, i.e., binning, essentially trading storage space for computing time.
2. SQL databases integer constraints on the data type of start and end positions exploit the computer's built-in optimization on native data type computing.
3. Clustered indices on SQL database tables optimize data retrieval operations, exploit locality of information properties, and reduce the number of data reads, thus significantly improve the speed of querying large datasets.
4. SQL servers have optimal implementations of set operations such as hashing and bitmaps for matching and sorting data.
5. The use of general purpose SQL database servers (e.g. Microsoft SQL Server 2005) exploits available built-in features such as multi-threading, caching, 64-bit architecture design, and memory allocation, etc. with no additional coding needed.

The RNA profiles including the genes pre-determined or transcriptionally active regions discovered and abundance scores generated from the system using the instantly claimed methods are quantitative and biologically significant. There are many known and potential utilities based on expression profiling analysis for the RNA profiles generated. The utilities include but are not limited to discovery of biomarker gene panel for diseases, discovery of new non-coding biomarker gene for diseases, and discovery of new biological functions for known genes.

In summary, the method and system disclosed herein can efficiently process sequencing output sequences for discovery of transcriptionally active regions and quantify the sequence abundances. The transcriptionally active region profiles generated by the system have many utilities based on RNA expression profiling.

EXAMPLE 1

Computational Identification of Human Intronic Sense EST (ISE) Hotspots Reveals Potential Functional RNA Elements Recent evidence suggests that a large portion of the mammalian genome is transcribed. Expressed sequence tags (ESTs) identified through large sequencing projects mark the transcribed regions of the genome. EST hotspots, genomic regions where many ESTs are mapped, may have significant biological functions and biomarker potential although many of them map to the non-coding portions of genes. The instantly claimed method applies a transcriptionally active region discovery algorithm to identify EST hotspots in the genome and to quantify their "hotness" by calculating an abundance score. Using the public dbEST data, the instant method was able to identify a set of human intronic sense EST (ISE) transcriptionally active regions, or "hotspots". The results show that the ISE transcriptionally active regions likely represent both coding and non-coding functional RNA elements.

Figure 4:
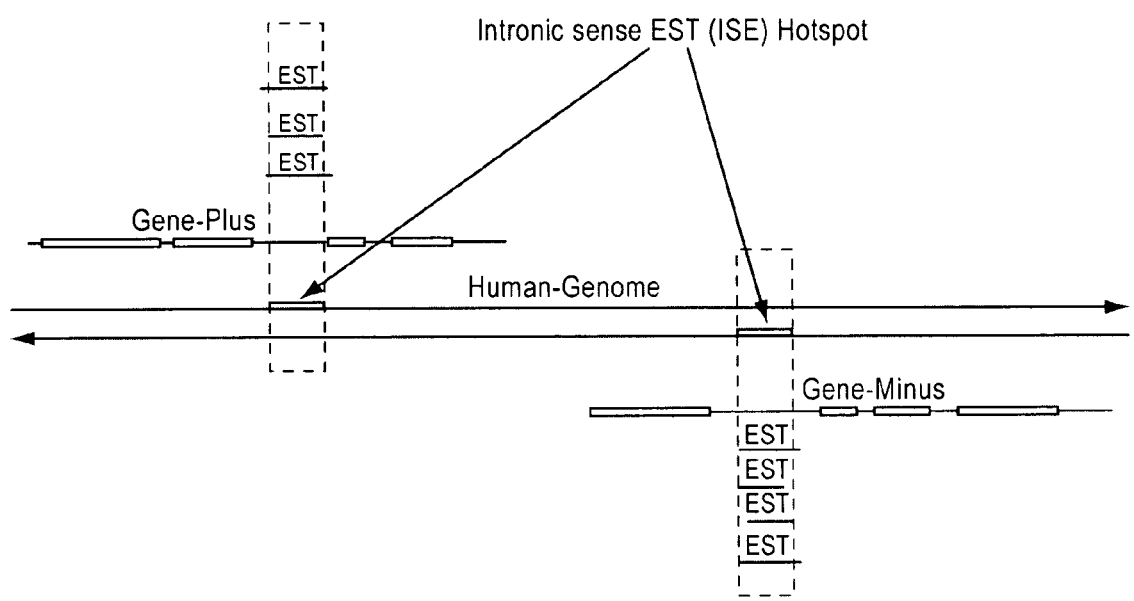
FIG. 4 illustrates the mapping of an intronic sense EST (ISE) transcriptionally active regions (also known as "hotspots").

An intronic sense EST (ISE) transcriptionally active region is defined as a contiguous genomic DNA fragment that maps to an intronic region of a known RefSeq annotated transcript and covered by at least three sense ESTs for each nucleotide position (FIG. 4).

The process for providing an abundance score calculation for a transcriptionally active region comprises identifying all RefSeq transcript variants for each Entrez Gene ID and collapsing exons of RefSeq transcript variants into one virtual transcript for each Entrez Gene ID. Consensus introns are then derived from the virtual transcript and all ESTs in the human dbEST that overlap the consensus intron are identified. The EST abundance coverage for each nucleotide in the consensus intron are calculated and contiguous regions with length>=20 nts and EST coverage>=3 are identified as ISE transcriptionally active regions. Finally, an abundance score (AS), or "hotness", is calculated for each transcriptionally active region as follows:

$$AS = \frac{\text{Sum of coverage count for each nucleotide in the transcription active region}}{\text{Length of the transcription active region}}$$

Figures 5A, 5B:
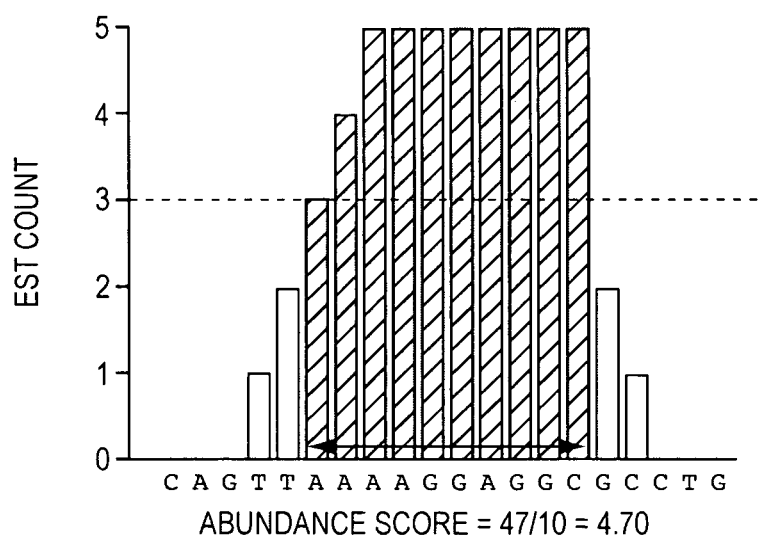
FIG. 5 illustrates the Abundance Score, also known as "hotness", calculation (SEQ ID NOS 10-13, respectively in order of appearance).

FIGS. 3 and 5 illustrate how a transcriptionally active region is identified and its AbundanceScore calculated using the sequence alignments described above.

As shown in Table 1, most ISE transcriptionally active regions overlap predicted regions from two UCSC Genome Browser tracks (Karolchik et al., 2003): 1) ECGene track, predicts spliced gene exons enriched in coding sequences, and 2) 7× Reg Potential track, predicts mostly regulatory non-coding sequences. Thus ISE transcriptionally active regions may represent potential functional RNA elements (defined as genomic sequences coding for functional RNA transcripts). These functional RNA elements may be coding or non-coding regulatory sequences.

TABLE 1

Human ISE transcriptionally active regions

Number of human ISE transcriptionally active regions identified: 81,342
Number of Entrez genes having ISE transcriptionally active regions: 12,406
Median length of human ISE transcriptionally active regions: 124
Median Hotness of human ISE transcriptionally active regions: 3.28
Number of ESTs in human dbESTs screened: ~7.3 million
Reference human genome assembly: NCBI 35 (UCSC HG17)
Most ISE transcriptionally active regions overlap with UCSC Genome Browser ECGene regions Number of human ISE transcriptionally active regions overlapping ECGene predicted exons: 63,361
Median overlap length: 119 nts
Median percentage of ECGene exons overlapping ISE transcriptionally active regions: 23%
Median percentage of ISE transcriptionally active regions overlapping ECGene exons: 100%
Median Hotness for the ISE transcriptionally active regions overlapping ECGene exons: 3.89
Most ISE transcriptionally active regions overlap with UCSC Genome Browser 7X Reg Potential regions Number of human ISE transcriptionally active regions overlapping 7x Reg Potential predicted regions: 60,900
Median overlap length: 108 nts
Median percentage of 7x Reg Potential regions overlapping ISE hotspots: 13%
Median percentage ISE hotspots overlapping 7x Reg Potential regions: 100%
Median Hotness for the ISE hotspots overlapping 7x Reg Potential regions: 3.60

When ESTs align exactly with clean sharp edges, the resulting transcriptionally active regions will have an integer abundance score (FIG. 6). If ESTs are staggered when aligned, the abundance score for the transcriptionally active region will most likely result in a decimal that distances an integer. Given the minimal length cutoff of 20 nucleotides and abundance score cutoff of 3, by our calculation a typical ISE transcriptionally active region has a random chance of less than 0.003 to have integer abundance score.

Figure 7A:
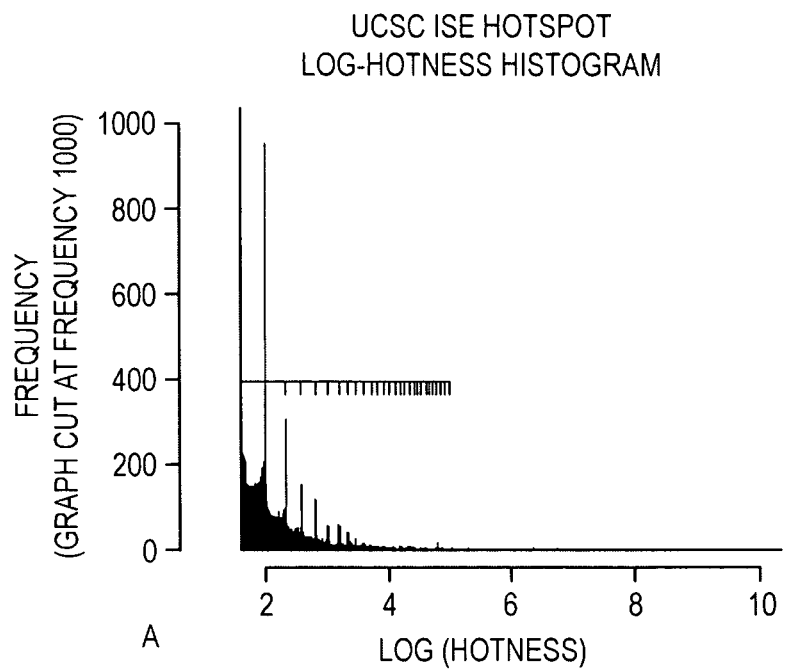
FIG. 7 illustrates abundance score distributions for the ISE transcriptionally active regions (a) and exons in RefSeq (b).
Figure 7B:
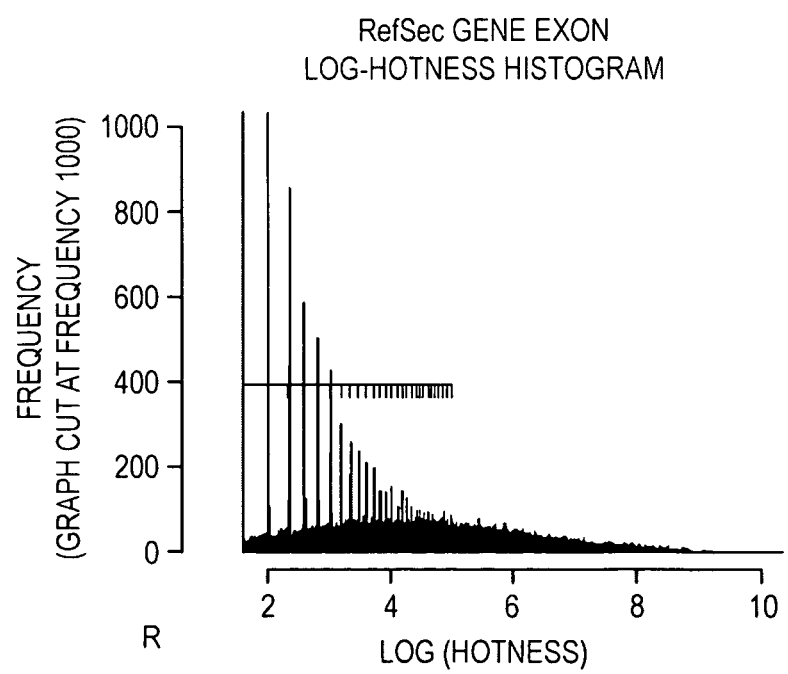

FIGS. 7A and B show abundance score distributions for the ISE transcriptionally active regions (A) and exons in RefSeq (B). The red ticks mark the location of integers ranging from 3 to 32 in log2 scale and indicate that the spikes are co-located around integers. The abundance score distribution is uneven and is significantly higher (indicated by the spikes in Figure A) around integers. Integer abundance scores are most likely products of clean sharp edged EST alignments, a prominent characteristic of coding RNA exons resulting from precise splicing control. Consistently, this uneven distribution is a characteristic shared with that of known exons in RefSeq (Figure B) transcripts. It indicates that many of these ISE transcriptionally active regions are potentially un-discovered exons. 19,532 ISE transcriptionally active regions were found to have abundance scores equal to or greater than 5.0, and 1462 of those have abundance scores very close to an integer (<=0.01 to the nearest integer). By this estimation, 7.49% of the ISE transcriptionally active regions are likely to be un-discovered exons. This estimation may be largely conservative given that only a small percentage of known RefGene exons have abundance scores close to integers. Since the ISE transcriptionally active regions are mapped into known gene intronic regions, these potentially are un-discovered alternatively spliced exons that may be tissue or cell specific for the known genes.

In summary, intronic sense EST (ISE) transcriptionally active regions represent potentially functional RNA elements in the genome. The functional RNA elements revealed by the ISE transcriptionally active regions may be coding or non-coding regulatory sequences.

EXAMPLE 2

In another example, an expression profile dataset for human tissues was generated from a proprietary sequencing dataset of approximately thirteen million ESTs. Recent evidence indicates that approximately 60% of the mammalian genome is transcribed. The transcribed RNA sequences can be effectively detected through large scale sequencing projects and outputted as expressed sequence tags (ESTs). ESTs mark the transcribed sequences in the genome, frequently map to noncoding regions, i.e., intronic or intergenic gene sequences. These non-coding ESTs may identify functional RNA elements that have significant biological function and biomarker potential. Thus there is a need for an efficient method to identify functional RNA elements through EST sequencing and data analysis.

In this example, an SQL database management system was utilized to create and implement an efficient algorithm that identifies transcriptionally active regions (TARs) in the genome and quantifies their abundances. Using our proprietary LifeSeq EST data, many TARs were identified in the known gene introns in human genome. Although gene introns have been considered as non-functional by conventional wisdom, the TARs discovered by this method along with their significant AbundanceScores indicate they are likely functional. By analysis of large scale tissue specific EST data, TARs were discovered that represent potential biomarkers to differentiate several tumor and normal samples (Tables 2-5).

TABLE 2

| Tar_Intestine_Small_Normal_Id | GeneIntronId | TarStart | TarEnd | TarAbundanceScore | chrom | strand | GeneId | symbol |
|---|---|---|---|---|---|---|---|---|
| 1 | 88 | 8716307 | 8716571 | 4.89 | chr16 | + | 18 | ABAT |
| 2 | 88 | 8730789 | 8730877 | 3 | chr16 | + | 18 | ABAT |
| 3 | 231 | 2322414 | 2322651 | 4.89 | chr16 | − | 21 | ABCA3 |
| 4 | 247 | 30647370 | 30647907 | 3 | chr6 | + | 23 | ABCF1 |
| 5 | 323 | 130763439 | 130763676 | 4 | chr9 | + | 25 | ABL1 |
| 6 | 347 | 133161298 | 133161407 | 3 | chr9 | − | 28 | ABO |
| 7 | 375 | 1006215 | 1006619 | 3 | chr17 | − | 29 | ABR |

TABLE 2-continued

| Tar_Intestine_Small_Normal_Id | GeneIntronId | TarStart | TarEnd | TarAbundanceScore | chrom | strand | GeneId | symbol |
|---|---|---|---|---|---|---|---|---|
| 8 | 549 | 7066909 | 7066934 | 3 | chr17 | + | 37 | ACADVL |
| 9 | 549 | 7066980 | 7067096 | 3 | chr17 | + | 37 | ACADVL |
| 10 | 549 | 7067113 | 7067174 | 3.52 | chr17 | + | 37 | ACADVL |
| 11 | 587 | 28953884 | 28954085 | 3 | chr17 | − | 40 | ACCN1 |
| 12 | 748 | 74037606 | 74037747 | 3.82 | chr2 | + | 72 | ACTG2 |
| 13 | 766 | 43901084 | 43901475 | 3 | chr19 | + | 81 | ACTN4 |
| 14 | 793 | 68418541 | 68418826 | 3 | chr14 | − | 87 | ACTN1 |
| 15 | 798 | 68423829 | 68424157 | 3.73 | chr14 | − | 87 | ACTN1 |
| 16 | 798 | 68424289 | 68424327 | 3 | chr14 | − | 87 | ACTN1 |
| 17 | 916 | 54300973 | 54301341 | 3 | chr2 | + | 98 | ACYP2 |
| 18 | 963 | 56770771 | 56771061 | 4.86 | chr15 | − | 102 | ADAM10 |
| 19 | 977 | 151384674 | 151385194 | 3.89 | chr1 | − | 103 | ADAR |

Normal tissue transcriptionally active regions: the genomic coordinates, abundance scores, and gene information for the transcriptionally active regions (TAR) found in the known gene intronic region sense strand from human normal small intestine tissue. Table only includes the first 20 rows in each sheet for this sample file for the small intestine tissue.

TABLE 3

| Tar_Intestine_Small_Tumor_Id | GeneIntronId | TarStart | TarEnd | TarAbundanceScore | chrom | strand | GeneId | symbol |
|---|---|---|---|---|---|---|---|---|
| 1 | 397 | 32574804 | 32575372 | 3 | chr17 | − | 31 | ACACA |
| 2 | 3754 | 209151625 | 209151791 | 3.48 | chr1 | + | 467 | ATF3 |
| 7 | 23402 | 44026130 | 44026273 | 3 | chr19 | − | 3191 | HNRPL |
| 8 | 25574 | 37765267 | 37765420 | 3.81 | chr3 | + | 3680 | ITGA9 |
| 9 | 29439 | 150758710 | 150758762 | 3.62 | chrX | + | 4103 | MAGEA4 |
| 11 | 36092 | 66697468 | 66697536 | 3 | chr13 | − | 5101 | PCDH9 |
| 13 | 41506 | 89695255 | 89695806 | 3 | chr10 | + | 5728 | PTEN |
| 14 | 44814 | 149805307 | 149805363 | 3 | chr5 | − | 6208 | RPS14 |
| 17 | 49786 | 29597976 | 29598032 | 3 | chr16 | + | 6818 | SULT1A3 |
| 18 | 49786 | 29613486 | 29613855 | 3 | chr16 | + | 6818 | SULT1A3 |
| 19 | 49786 | 29820280 | 29820470 | 3 | chr16 | + | 6818 | SULT1A3 |
| 29 | 49786 | 29994842 | 29994916 | 5.52 | chr16 | + | 6818 | SULT1A3 |
| 30 | 49786 | 29995137 | 29995297 | 6 | chr16 | + | 6818 | SULT1A3 |
| 31 | 49786 | 30000081 | 30000132 | 6 | chr16 | + | 6818 | SULT1A3 |
| 32 | 49786 | 30001306 | 30001356 | 5 | chr16 | + | 6818 | SULT1A3 |
| 33 | 49786 | 30001568 | 30001669 | 5 | chr16 | + | 6818 | SULT1A3 |
| 34 | 49786 | 30002216 | 30002389 | 4.55 | chr16 | + | 6818 | SULT1A3 |
| 35 | 49786 | 30002477 | 30002546 | 3.34 | chr16 | + | 6818 | SULT1A3 |
| 37 | 56510 | 31610906 | 31610959 | 3 | chr6 | − | 7919 | BAT1 |

Tumor tissue transcriptionally active regions: the genomic coordinates, abundance scores, and gene information for the transcriptionally active regions (TAR) found in the known gene intronic region sense strand from human Tumor small intestine tissue. Table only includes the first 20 rows in each sheet for this sample file for the small intestine tissue.

TABLE 4

| GeneIntronId | Normal_TarId | Normal_TarStart | Normal_TarEnd | Normal_TarAbundanceScore | Tumor_TarId | Tumor_TarStart | Tumor_TarEnd | Tumor_TarAbundanceScore | overlap-Length |
|---|---|---|---|---|---|---|---|---|---|
| 3858 | 51 | 8780574 | 8781266 | 11.08 | 3 | 8781040 | 8781245 | 3 | 206 |
| 12816 | 139 | 58233806 | 58234184 | 8.92 | 4 | 58233926 | 58233985 | 3 | 60 |
| 19424 | 227 | 144703744 | 144704531 | 17.95 | 5 | 144703749 | 144704430 | 10.16 | 682 |
| 20070 | 232 | 12865916 | 12866686 | 29.38 | 6 | 12865920 | 12866603 | 9.21 | 684 |
| 31679 | 458 | 233309165 | 233309488 | 8.66 | 10 | 233309185 | 233309471 | 3 | 287 |
| 39664 | 536 | 27527145 | 27528076 | 34.8 | 12 | 27527323 | 27528067 | 4.28 | 745 |
| 44833 | 598 | 80838027 | 80838128 | 42 | 15 | 80838128 | 80838694 | 6.24 | 625 |
| 46273 | 619 | 11959578 | 11960257 | 5.67 | 16 | 11959587 | 11959785 | 3 | 199 |
| 49786 | 721 | 29984597 | 29984749 | 18.46 | 20 | 29984606 | 29984749 | 8.82 | 144 |
| 49786 | 722 | 29986056 | 29986189 | 22.66 | 21 | 29986056 | 29986188 | 13.73 | 133 |
| 49786 | 723 | 29986272 | 29986483 | 7.88 | 22 | 29986272 | 29986483 | 14.43 | 212 |
| 49786 | 724 | 29987468 | 29987522 | 16.02 | 23 | 29987468 | 29987522 | 12.31 | 55 |
| 49786 | 725 | 29987640 | 29987800 | 15.53 | 24 | 29987640 | 29987800 | 12.55 | 161 |
| 49786 | 726 | 29988128 | 29988211 | 9.94 | 25 | 29988128 | 29988211 | 7.69 | 84 |
| 49786 | 727 | 29988321 | 29988495 | 12.49 | 26 | 29988321 | 29988495 | 7.21 | 175 |
| 49786 | 728 | 29988652 | 29988851 | 15.13 | 27 | 29988652 | 29988851 | 6.09 | 200 |
| 49786 | 729 | 29988939 | 29989233 | 6.82 | 28 | 29988939 | 29989193 | 4.87 | 255 |
| 53627 | 807 | 148342968 | 148343285 | 18.24 | 36 | 148342976 | 148343528 | 4.81 | 310 |
| 58366 | 867 | 59663510 | 59663888 | 8.92 | 39 | 59663630 | 59663689 | 3 | 60 |

Overlapping transcriptionally active regions: the genomic coordinates, abundance scores, and gene information for the overlapping transcriptionally active regions (TAR) found in the known gene intronic region sense strand between human Normal and Tumor small intestine tissues. Table only includes the first 20 rows in each sheet for this sample file for the small intestine tissue.

The overlapping transcriptionally active regions (TARs) identified in Table 4 are likely to be constitutively expressed in small intestine tissue and may be used as the references for normalization in the expression profiling analysis.

Table 5 is a summary of all the TARs compiled from the complete datasets for the above study with abundance score greater or equal to 3.

TABLE 5

| Tissue Type | Number of TARs in Normal Tissue | Number of TARs in Tumor Tissue | Comon TARs overlapping between Normal and Tumor tissues |
|---|---|---|---|
| Breast | 1339 | 1589 | 488 |
| Large intestine | 1348 | 1462 | 517 |
| Small intestine | 2722 | 76 | 150 |
| Prostate | 1126 | 2395 | 496 |
| Skin | 1083 | 1828 | 894 |

A subset of TARs were selected for our colon and breast cancer biomarker screen according to further examination of public literature and proprietary gene data (Table 6).

The TARs shown in Table 6 represent tissue specific biomarkers (e.g., biomarkers for differentiations between normal and tumor breast tissues, or normal and tumor colon tissues), and can be utilized as diagnostic or prognostic markers of cancer.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

TABLE 6

| GeneIntronId | TarStart | TarEnd | AbundanceScore | Length | Chromosome | Strand | Official Gene Symbol | GeneID |
|---|---|---|---|---|---|---|---|---|
| Breast_Normal | | | | | | | | |
| B_N_1 | ... | ... | 26.07 | 248 | chr1 | − | XXXXX | 123456 |
| B_N_2 | ... | ... | 15.76 | 631 | chr5 | − | XXXXX | 123456 |
| B_N_3 | ... | ... | 15.71 | 563 | chr3 | − | XXXXX | 123456 |
| B_N_4 | ... | ... | 15.49 | 827 | chr7 | + | XXXXX | 123456 |
| B_N_5 | ... | ... | 15.09 | 127 | chr16 | + | XXXXX | 123456 |
| B_N_6 | ... | ... | 14.44 | 459 | chr8 | − | XXXXX | 123456 |
| Breast_Tumor | | | | | | | | |
| B_T_1 | ... | ... | 46.22 | 493 | chr3 | + | XXXXX | 123456 |
| B_T_2 | ... | ... | 24.00 | 99 | chr16 | + | XXXXX | 123456 |
| B_T_3 | ... | ... | 23.86 | 79 | chr16 | + | XXXXX | 123456 |
| B_T_4 | ... | ... | 19.61 | 272 | chr3 | + | XXXXX | 123456 |
| B_T_5 | ... | ... | 16.32 | 1027 | chr17 | + | XXXXX | 123456 |
| B_T_6 | ... | ... | 14.28 | 224 | chr11 | + | XXXXX | 123456 |
| B_T_7 | ... | ... | 14.13 | 311 | chr1 | + | XXXXX | 123456 |
| B_T_8 | ... | ... | 14.02 | 1067 | chr6 | + | XXXXX | 123456 |
| B_T_9 | ... | ... | 13.76 | 792 | chr9 | + | XXXXX | 123456 |
| B_T_10 | ... | ... | 13.75 | 739 | chr11 | + | XXXXX | 123456 |
| Colon_Normal | | | | | | | | |
| C_N_1 | ... | ... | 38.72 | 208 | chr1 | + | XXXXX | 123456 |
| C_N_2 | ... | ... | 37.26 | 327 | chr16 | + | XXXXX | 123456 |
| C_N_3 | ... | ... | 28.74 | 664 | chr16 | + | XXXXX | 123456 |
| C_N_4 | ... | ... | 28.69 | 360 | chr2 | − | XXXXX | 123456 |
| C_N_5 | ... | ... | 22.95 | 159 | chr16 | + | XXXXX | 123456 |
| C_N_6 | ... | ... | 18.17 | 446 | chr6 | + | XXXXX | 123456 |
| C_N_7 | ... | ... | 17.20 | 492 | chr12 | − | XXXXX | 123456 |
| C_N_8 | ... | ... | 16.83 | 467 | chr19 | − | XXXXX | 123456 |
| C_N_9 | ... | ... | 16.63 | 150 | chr14 | + | XXXXX | 123456 |
| Colon_Tumor | | | | | | | | |
| C_T_1 | ... | ... | 43.00 | 97 | chr20 | + | XXXXX | 123456 |
| C_T_2 | ... | ... | 24.92 | 620 | chr2 | + | XXXXX | 123456 |
| C_T_3 | ... | ... | 20.07 | 234 | chr19 | + | XXXXX | 123456 |
| C_T_4 | ... | ... | 19.24 | 269 | chrX | − | XXXXX | 123456 |
| C_T_5 | ... | ... | 13.03 | 511 | chr19 | + | XXXXX | 123456 |
| C_T_6 | ... | ... | 12.33 | 249 | chr5 | + | XXXXX | 123456 |
| C_T_7 | ... | ... | 11.6 | 279 | chr10 | − | XXXXX | 123456 |
| C_T_8 | ... | ... | 11.31 | 251 | chr5 | − | XXXXX | 123456 |
| C_T_9 | ... | ... | 11.19 | 881 | chr18 | + | XXXXX | 123456 |

Gene symbols and specific identifiers have been masked out.

The invention claimed is:

1. A computer-implemented method for determining a quantitative measure for an RNA expression profile of a biological sample containing sequences of nucleotides, the method comprising:
for each of a plurality of output sequences from the biological sample:
receiving, information of an alignment of the respective output sequence onto a reference sequence that has a nucleotide at each of a plurality of nucleotide positions, the alignment aligning the output sequences to specific nucleotide positions of the reference sequence, wherein at least a portion of the output sequences are derived from RNA, and wherein the reference sequence includes at least a portion of a genome;
calculating a count histogram for the reference sequence based on the alignment of the plurality of output sequences onto the reference sequence, the count histogram including a respective coverage count for each nucleotide position of the reference sequence, wherein calculating the count histogram includes:
for each nucleotide position of the reference sequence:
determining, the corresponding coverage count for the respective nucleotide position by determining the number of output sequences that align to the respective nucleotide position of the reference sequence;
locating a first contiguous region in the count histogram where the coverage count for each nucleotide position in the first contiguous region is equal to or greater than a threshold; and
calculating a first abundance score for the first contiguous region, wherein an abundance score includes an average of the coverage count for each nucleotide position in a contiguous region; wherein the method is performed by a computer.

2. The computer-implemented method of claim 1, further comprising:
identifying the first contiguous region of the plurality of nucleotide positions of the reference sequence as being a transcriptionally active region.

3. The computer-implemented method of claim 2, further comprising
using the identified transcriptionally active region as a biomarker to differentiate between different types of biological samples.

4. The computer-implemented method of claim 3, wherein the different types of biological samples include tumor and normal samples.

5. The computer-implemented method of claim 1, wherein the threshold is a fractional number.

6. The computer-implemented method of claim 1, wherein the first contiguous region of the reference sequence is required to be equal to or greater than a minimum length.

7. The computer-implemented method of claim 6, wherein the minimum length is 20 nucleotides, and wherein the threshold is greater than or equal to three.

8. The computer-implemented method of claim 1, wherein the first abundance score is calculated as a sum of all the coverage counts for the first contiguous region divided by the length of the first contiguous region, and wherein the length is the number of nucleotide positions in the first contiguous region.

9. The computer-implemented method of claim 1, wherein the human genome is used as the reference sequence.

10. The computer-implemented method of claim 1, wherein the reference sequence is a predetermined target gene sequence for which the RNA expression profile is being determined.

11. The computer-implemented method of 10, wherein the threshold is zero for the predetermined target gene sequence.

12. The computer-implemented method of claim 1, wherein the reference sequence is assembled from a consensus of the output sequences.

13. The computer-implemented method of claim 1, further comprising:
determining a second coverage count for each of the nucleotide positions of the reference sequence using second output sequences from a different biological sample;
locating a second contiguous region of the plurality of nucleotide positions where the second coverage count for each nucleotide position is equal to or greater than the threshold;
calculating a second abundance score for the second contiguous region;
comparing the first abundance score to the second abundance score; and
determining that one of the biological samples is a disease sample based on the comparison.

14. The computer-implemented method of claim 13, further comprising:
identifying the second contiguous region for comparison to the first contiguous region by determining an overlap between the first contiguous region and the second contiguous region.

15. The computer-implemented method of claim 14, wherein determining an overlap between the first contiguous region and the second contiguous region includes:

representing each of the first contiguous region and the second contiguous region with reference coordinates based on nucleotide positions of an alignment to the reference sequence, wherein the reference coordinates include sequence start and end positions; and comparing the start and end positions of the first contiguous region to the start and end positions of the second contiguous region.

16. The computer-implemented method of claim 15, wherein the reference coordinates of a contiguous region are implemented with the start position less than or equal to the end position, or with the start position always greater than or equal to the end position.

17. The computer-implemented method of claim 15, wherein the reference coordinates are comprised of a chromosome location, strand, a start position and an end position according to an alignment onto the reference sequence.

18. The computer-implemented method of claim 17, wherein the chromosome location of the first contiguous region equals the chromosome location of the second contiguous region, and wherein the strand of the first contiguous region equals the strand of the second contiguous region.

19. The computer-implemented method of claim 15, wherein a minimum overlap length is required for a determination that the first contiguous region and the second contiguous region overlap.

20. The computer-implemented method of claim 1, further comprising:
determining an overlap between the first contiguous region and another sequence of nucleotides by:
representing each of the first contiguous region and the another sequence with reference coordinates based on nucleotide positions of an alignment to the reference sequence, wherein the reference coordinates include sequence start and end positions; and
comparing the start and end positions of the first contiguous region to the start and end positions of the another sequence; and
if an overlap exists, associating the first contiguous region with the another sequence.

21. The computer-implemented method of claim 20, wherein the reference coordinates are comprised of a chromosome location, strand, a start position and an end position according to an alignment onto the reference sequence.

22. The computer-implemented method of claim 20, wherein a minimum overlap length is required for a determination that the first contiguous region and the another sequence overlap.

23. A system for determining a quantitative measure for an RNA expression profile of a biological sample containing sequences of nucleotides, the system comprising:
a database storing, for each of a plurality of output sequences from the biological sample:
information of an alignment of the respective output sequence onto a reference sequence that has a nucleotide at each of a plurality of nucleotide positions, the alignment aligning the output sequences to specific nucleotide positions of the reference sequence, wherein at least a portion of the output sequences are derived from RNA, and wherein the reference sequence includes at least a portion of a genome; and
one or more processors that are communicably coupled with the database and that are programmed to:
calculate a count histogram for the reference sequence based on the alignment of the plurality of output sequences onto the reference sequence, the count histogram including a respective coverage count for each nucleotide position of the reference sequence, wherein calculating the count histogram includes:
for each nucleotide position of the reference sequence:
determine the corresponding coverage count for the respective nucleotide position by determining the number of output sequences that align to the respective nucleotide position of the reference sequence;
locate a first contiguous region in the count histogram where the coverage count for each nucleotide position in the first contiguous region is equal to or greater than a threshold; and
calculate a first abundance score for the first contiguous region, wherein an abundance score includes an average of the coverage count for each nucleotide position in a contiguous region.

24. The system of claim 23, wherein the one or more processors are further programmed to:
determine a second coverage count for each of the nucleotide positions of the reference sequence using second output sequences from a different biological sample;
locate a second contiguous region of the plurality of nucleotide positions where the second coverage count for each nucleotide position is equal to or greater than the threshold;
calculate a second abundance score for the second contiguous region;
compare the first abundance score to the second abundance score; and
determine that one of the biological samples is a disease sample based on the comparison.

25. The system of claim 23, further comprising:
a computer output device that is coupled with the one or more processors and that displays the first contiguous region with the first abundance score.

26. A computer-implemented method for determining a transcriptionally active region of a reference sequence associated with a biological sample containing sequences of nucleotides, the method comprising:
for each of a plurality of output sequences from the biological sample:
receiving, information of an alignment of the respective output sequence onto a reference sequence that has a nucleotide at each of a plurality of nucleotide positions, the alignment aligning the output sequences to specific nucleotide positions of the reference sequence, wherein at least a portion of the output sequences are derived from RNA, and wherein the reference sequence includes at least a portion of a genome;
calculating a count histogram for the reference sequence based on the alignment of the plurality of output sequences onto the reference sequence, the count histogram including a respective coverage count for each nucleotide position of the reference sequence, wherein calculating the count histogram includes:
for each nucleotide position of the reference sequence:
determining, the corresponding coverage count for the respective nucleotide position by determining the number of output sequences that align to the respective nucleotide position of the reference sequence;
locating a first contiguous region in the count histogram where the coverage count for each nucleotide position in the first contiguous region is equal to or greater than a threshold; and identifying the first contiguous region of the plurality of nucleotide positions of the reference sequence as being a transcriptionally active region; wherein the method is performed by a computer.

27. The computer-implemented method of claim 26, further comprising
using the identified transcriptionally active region as a biomarker to differentiate between different types of biological samples.

28. The computer-implemented method of claim 27, wherein the different types of biological samples include tumor and normal samples.

29. The computer-implemented method of claim 26, wherein the first contiguous region of the reference sequence is required to be equal to or greater than a minimum length.

30. The computer-implemented method of claim 29, wherein the minimum length is 20 nucleotides, and wherein the threshold is greater than or equal to three.

31. The computer-implemented method of claim 26, wherein the human genome is used as the reference sequence.

32. The computer-implemented method of claim 26, wherein the reference sequence is a predetermined target gene sequence for which the RNA expression profile is being determined.

33. The computer-implemented method of claim 32, wherein the threshold is zero for the predetermined target gene sequence.

34. The computer-implemented method of claim 26, wherein the reference sequence is assembled from a consensus of the output sequences.

35. The computer-implemented method of claim 26, further comprising:
determining an overlap between the first contiguous region and another sequence of nucleotides by:
representing each of the first contiguous region and the another sequence with reference coordinates based on nucleotide positions of an alignment to the reference sequence, wherein the reference coordinates include sequence start and end positions; and
comparing the start and end positions of the first contiguous region to the start and end positions of the another sequence; and
if an overlap exists, associating the first contiguous region with the another sequence.

36. The computer-implemented method of claim 35, wherein the reference coordinates are comprised of a chromosome location, strand, a start position and an end position according to an alignment onto the reference sequence.

37. The computer-implemented method of claim 35, wherein a minimum overlap length is required for a determination that the first contiguous region and the another sequence overlap.

38. A system for determining a transcriptionally active region of a reference sequence associated with a biological sample containing sequences of nucleotides, the system comprising:
a database storing, for each of a plurality of output sequences from the biological sample:
information of an alignment of the respective output sequence onto a reference sequence that has a nucleotide at each of a plurality of nucleotide positions, the alignment aligning the output sequences to specific nucleotide positions of the reference sequence, wherein at least a portion of the output sequences are derived from RNA, and wherein the reference sequence includes at least a portion of a genome; and
one or more processors that are communicably coupled with the database and that are programmed to:
calculate a count histogram for the reference sequence based on the alignment of the plurality of output sequences onto the reference sequence, the count histogram including a respective coverage count for each nucleotide position of the reference sequence, wherein calculating the count histogram includes:
for each nucleotide position of the reference sequence:
determine the corresponding coverage count for the respective nucleotide position by determining the number of output sequences that align to the respective nucleotide position of the reference sequence;
locate a first contiguous region in the count histogram where the coverage count for each nucleotide position in the first contiguous region is equal to or greater than a threshold; and
identify the first contiguous region of the plurality of nucleotide positions of the reference sequence as being a transcriptionally active region.

39. The system of claim 38, further comprising:
a computer output device that is coupled with the one or more processors and that displays the first contiguous region as being a transcriptionally active region.

* * * * *

SEQUENCE LISTING

<160> NUMBER OF SEQ ID NOS: 13

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
caaagaaatc cagcgtcact aggtcagcta agccgaa                              37

<210> SEQ ID NO 2
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggcacaaaga atccagcgt cactaggtca gctaagccga aaaatgt                    47

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
atgtgtgcct gcgctcctcg cctcatcgat gacat                                35

<210> SEQ ID NO 4
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tccagcgtca ctaggtcagc taagccgaaa aatgtgtgcc tgcgctcctc gcctcatcga     60
t                                                                     61

<210> SEQ ID NO 5
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggtcagctaa gccgaaaaat gtgtgcctgc gctcctcgcc tcatcgatga c              51

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 6
gctaagccga aaaatgtgtg cctgcgc                                27

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tcactaggtc agctaagccg aaaaa                                  25

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tgtgcctgcg ctcctcgcct catc                                   24

<210> SEQ ID NO 9
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggcacaaaga aatccagcgt cactaggtca gctaagccga aaatgtgtg cctgcgctcc     60 tcgcctcatc gatgacat                                                  78

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
taaaaggagg cg                                                12

<210> SEQ ID NO 11
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aaaaggaggc gc                                                12

<210> SEQ ID NO 12
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 12
ttaaaaggag gc                                                              12

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cagttaaaag gaggcgcctg                                                      20
```